United States Patent [19]
Norris

[11] Patent Number: 5,592,289
[45] Date of Patent: Jan. 7, 1997

[54] SELF-ALIGNING MECHANISM FOR POSITIONING ANALYTE RECEPTACLES

[75] Inventor: Michael C. Norris, Los Gatos, Calif.

[73] Assignee: Molecular Dynamics, Sunnyvale, Calif.

[21] Appl. No.: 370,486

[22] Filed: Jan. 9, 1995

[51] Int. Cl.⁶ .................................................. G01N 21/01
[52] U.S. Cl. ........................ 356/244; 422/104; 436/809
[58] Field of Search .................................. 356/244, 246, 356/440, 399; 250/576; 436/165, 809; 422/101, 102, 186, 109, 104; 359/391, 392, 396, 393

[56] References Cited

U.S. PATENT DOCUMENTS

| | | | |
|---|---|---|---|
| 3,999,866 | 12/1976 | Mathisen | 356/244 |
| 4,159,875 | 7/1979 | Hauser | 356/244 |
| 4,431,924 | 2/1984 | Suovaniemi et al. | 356/244 |

OTHER PUBLICATIONS

Bio–Rad Laboratories, Inc. "Mini–Protean® II System" (brochure), Bulletin 1819 US, 1993. No Month.
Jule Inc. Biotechnologies brochure "Snap-A-Gel™ Precast Gels" (brochure), Jule, Inc., May 1994.

*Primary Examiner*—Hoa Q. Pham
*Attorney, Agent, or Firm*—Blakely, Sokoloff, Taylor & Zafman

[57] ABSTRACT

A self-aligning mechanism for positioning analyte receptacles comprises a loading carriage which bears a tray. In one embodiment, the carriage is slidingly mounted in a structure and includes three guide pins and a stop pin. In this embodiment, the tray has a leaf spring attached at the rear thereof, a lateral protuberance for contacting the structure, and two frontal and one lateral oblique slots. A pair of vertical contact planes, orthogonally disposed with respect to each other, are formed on the top surface of the tray.

20 Claims, 8 Drawing Sheets

SELF-ALIGNING MECHANISM FOR POSITIONING ANALYTE RECEPTACLES

BACKGROUND OF THE INVENTION

1. Field of the Invention

The present invention relates to positioning mechanisms, particularly to an apparatus for positioning receptacles which contain analyte samples to be assayed by a measuring instrument, such as a photometer.

2. Description of Related Art

At the present time, various instruments are used to measure photometric properties, such as color, absorbance, intensity, and photo-luminescence, in specific locations of organic, inorganic, and biological samples located in analyte receptacles, e.g., cuvettes. For example, photometers are commonly utilized in biological research to test specimens for various chemicals, hormones, and enzymes. It is well known in the art that proper alignment of the container holding the analyte samples and the light beam of the photometer is necessary to perform many photometric measurements. Similarly, to perform image analysis, devices such as gel scanners and microscopes demand sample stages that provide consistent and accurate positioning of the analyte receptacle, e.g., a glass slide. In these applications, repeatable positioning of the analyte receptacle is also important for re-analysis of the image. Moreover, for imaging devices that utilize electrophoresis gels, alignment of these gels with respect to the electrophoreses axis is critical for consistent measurements.

Many photometric instruments make discrete measurements using multisite analyte receptacles called "microplates", which generally comprise rectangular structures made of glass or plastic, each having a multiplicity of wells (e.g. cylindrical wells) for holding analyte samples. A microplate allows preparation of a large number of test samples and may contain twenty four, forty eight, ninety six, or any other number of wells. Microplates are inexpensive, safe, sturdy, and convenient to handle. They are disposable, but can be cleaned easily and may be reused when necessary.

FIG. 1 illustrates one of the mechanisms currently available for positioning analyte receptacles, such as microplates, with respect to a measuring instrument. This mechanism comprises a carriage 100, slidingly mounted in an enclosure 102 that houses a measuring instrument, e.g., a photometer (not shown). A through rectangular opening 104, formed in carriage 100, accommodates an analyte receptacle 108. FIG. 2 shows, from a top view, an analyte receptacle 108 sitting in carriage 100. Analyte receptacle 108 contains a plurality of wells 109 for holding analyte samples and has reference planes 103, 105, 110, and 112. Carriage 100 contains a pair of compression springs 106 and 107 used to align analyte receptacle 108 in carriage 100. As illustrated in FIG. 2, when analyte receptacle 108 is inserted into rectangular opening 104 of carriage 100, the force of compression springs 106 and 107 directed against reference planes 105 and 103 respectively, aligns reference planes 110 and 112 of analyte receptacle 108 against the planar inner walls 114 and 116, respectively, of rectangular opening 104. In this position, a portion of the bottom of analyte receptacle 108 rests on a lip 101 which surrounds the rectangular opening 104.

The above-described apparatus, however, possesses several salient flaws. Specifically, to insert analyte receptacle 108 into carriage 100, the resistance of compression springs 106 and 107 must be overcome. As a result, analyte receptacle 108 suddenly snaps into position as the spring resistance is surmounted. The abrupt movement of analyte receptacle 108 may cause the contents of wells 109 to spill out, contaminating adjacent wells and making accurate measurements impossible.

For the above-mentioned reason, robotic insertion of analyte receptacle 108 into carriage 100 is difficult. A precisely-directed positioning force, capable of preventing sudden movements of analyte receptacle 108 and overcoming the resistance of springs 106 and 107 is required for this task. Most reasonably-priced robotic placement mechanisms possess a degree of error that makes them inadequate for reliably inserting analyte receptacle 108 into carriage 100.

Should the samples located in wells 109 become misaligned with respect to the measuring and/or viewing instrument, the instrument will not be able to accurately perform the required measurements and/or viewing tasks. The apparatus of FIG. 1 is deficient in its reliance on the control of the shape of analyte receptacle 108 for accurate alignment thereof with the scanning mechanism of the measuring instrument. Careful control of the shape of analyte receptacle requires a potentially expensive, precise manufacturing process. It is apparent from FIG. 2 that alignment of analyte receptacle 108 is achieved through aligning its reference planes 110 and 112 with planar inner walls 114 and 116. Since whole surfaces of inner walls 114 arid 116 are being used as reference planes, imperfections anywhere on the surfaces of reference planes 110 and 112 (e.g. a bump) will result in misalignment of analyte receptacle 108 with respect to the measuring instrument. Moreover, extraneous particles may become trapped between reference planes 110 and 112 of analyte receptacle 108 and planar inner walls 114 and 116 of rectangular opening 104, further hampering the alignment accuracy.

As each analyte sample decreases in size and as the number of analyte samples on a particular analyte receptacle increases, alignment of the samples relative to the measuring instrument becomes critical. Currently, silicon wafers find growing use as analyte receptacles for such procedures as drug discovery, where a large number of test sites is required. For example, when it is necessary to identify a specific protein sequence for binding with a certain type of receptor, a high density of samples in the analyte receptacle (that is, a large number of analyte samples on a particular analyte receptacle) is needed to expose the receptor to as many different permutations of proteins as possible. Therefore, in this example, the samples to be assayed are located on the surface of a silicon wafer in a multitude of discreet microscopic locations, with each discreet microscopic location containing a single microscopic sample. The centers of these microscopic samples are generally positioned approximately 50 microns away from each other, thus allowing one to place about 40,000 assays in an area of one square centimeter. Because of the small size and close spacing of the analyte samples, the wafer must be precisely aligned with respect to the measuring apparatus, thus allowing the measuring apparatus to make error-free measurements of the samples.

SUMMARY OF THE INVENTION

It is accordingly desirable to provide a positioning mechanism for specimens to be assayed by a measuring instrument, such as a photometer, where the positioning mechanism overcomes the foregoing drawbacks, e.g., requires no force for insertion therein of a receptacle containing the analyte samples to be assayed, allows such insertion to be reliably implemented by conventional and inexpensive robotic mechanisms, and provides accurate alignment of the analyte receptacle, e.g., a microplate or a silicon wafer, with respect to the measuring instrument performing the assays.

It is also desirable for the positioning mechanism to be able to accommodate analyte receptacles of various configurations and to supply information about the configuration of a particular receptacle to a computer that controls the operation of the measuring instrument, thus making it possible to use an existing set of instructions stored in the computer's memory to control the measuring sequence of the instrument and to control the positioning of the measuring instrument relative to the analyte samples in the receptacle.

Further advantages of the invention will become apparent after consideration of the ensuing description and the accompanying drawings.

In its preferred embodiment, the positioning mechanism of the present invention comprises a loading carriage, which carries a tray. The loading carriage is slidingly mounted in a structure (which may be an enclosure) and includes two guide pins situated along the front of the loading carriage, one guide pin located along the side of the loading carriage, and one stop pin positioned at the rear thereof.

The tray has a leaf spring attached at the rear thereof, a lateral protuberance for contacting the enclosure, and two frontal and one lateral oblique slots. A pair of vertical contact planes, orthogonally disposed with respect to each other, are formed on the top surface of the loading tray. One of the contact planes includes a cavity, which houses a spring-loaded contact element, protruding therefrom.

The oblique slots of the tray are slidingly coupled with the guide pins of the carriage. When the carriage is fully protracted from the structure or enclosure, the lateral protuberance of the tray contacts the structure or enclosure, thus displacing the tray along the guide pins to the left and rearward with respect to the loading carriage. The guide pins cannot fully engage their corresponding oblique slots when the loading carriage is in a protracted position (such that the guide pins are relatively distant from the contact planes of the tray), thus providing sufficient room for an analyte receptacle to be inserted into the tray.

As the loading carriage is retracted into the structure or enclosure, contact between the structure or enclosure and the lateral protuberance of the tray is lost, thus allowing the leaf spring of the tray, preloaded against the stop pin of the loading carriage, to push the tray along the guide pins to the right and forward with respect to the loading carriage. This motion of the tray with respect to the loading carriage forces the orthogonal contact planes of the tray and the spring-loaded contact element against a corner of the analyte receptacle, thereby automatically aligning two reference planes of the analyte receptacle with the three guide pins of the loading carriage.

BRIEF DESCRIPTION OF THE DRAWINGS

The present invention is illustrated by way of example, and not by way of limitation, in the figures of the accompanying drawings, where.

For purposes of illustration, these figures are not necessarily drawn to scale. In all of the figures, like components are designated by like reference numerals.

DETAILED DESCRIPTION OF THE INVENTION

Throughout the following description, specific details are set forth in order to provide a more thorough understanding of the invention. However, the invention may be practiced without these particulars. In other instances, well known elements have not been shown or described to avoid unnecessarily obscuring the present invention. Accordingly, the specification and drawings are to be regarded in an illustrative, rather than a restrictive, sense.

Figure 1:
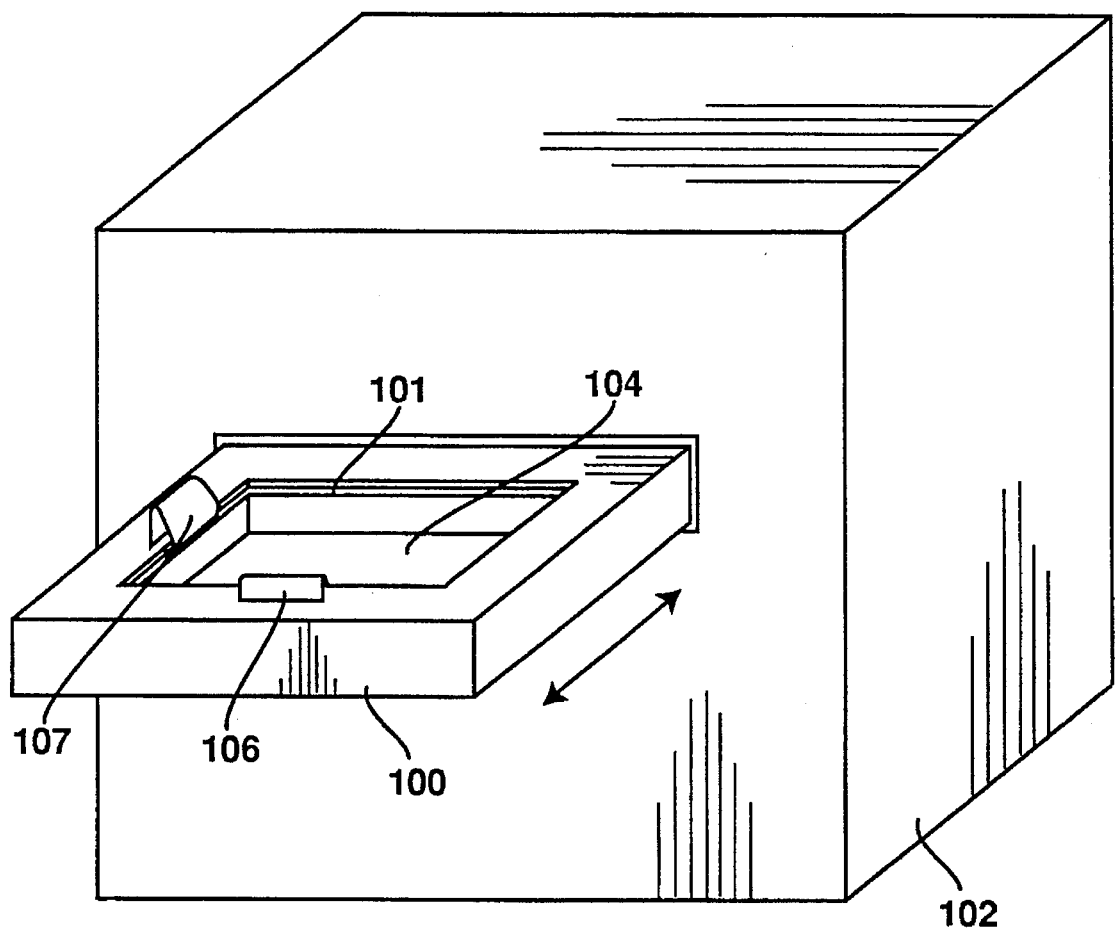
FIG. 1 is a perspective view of a prior-art positioning mechanism.
Figure 2:
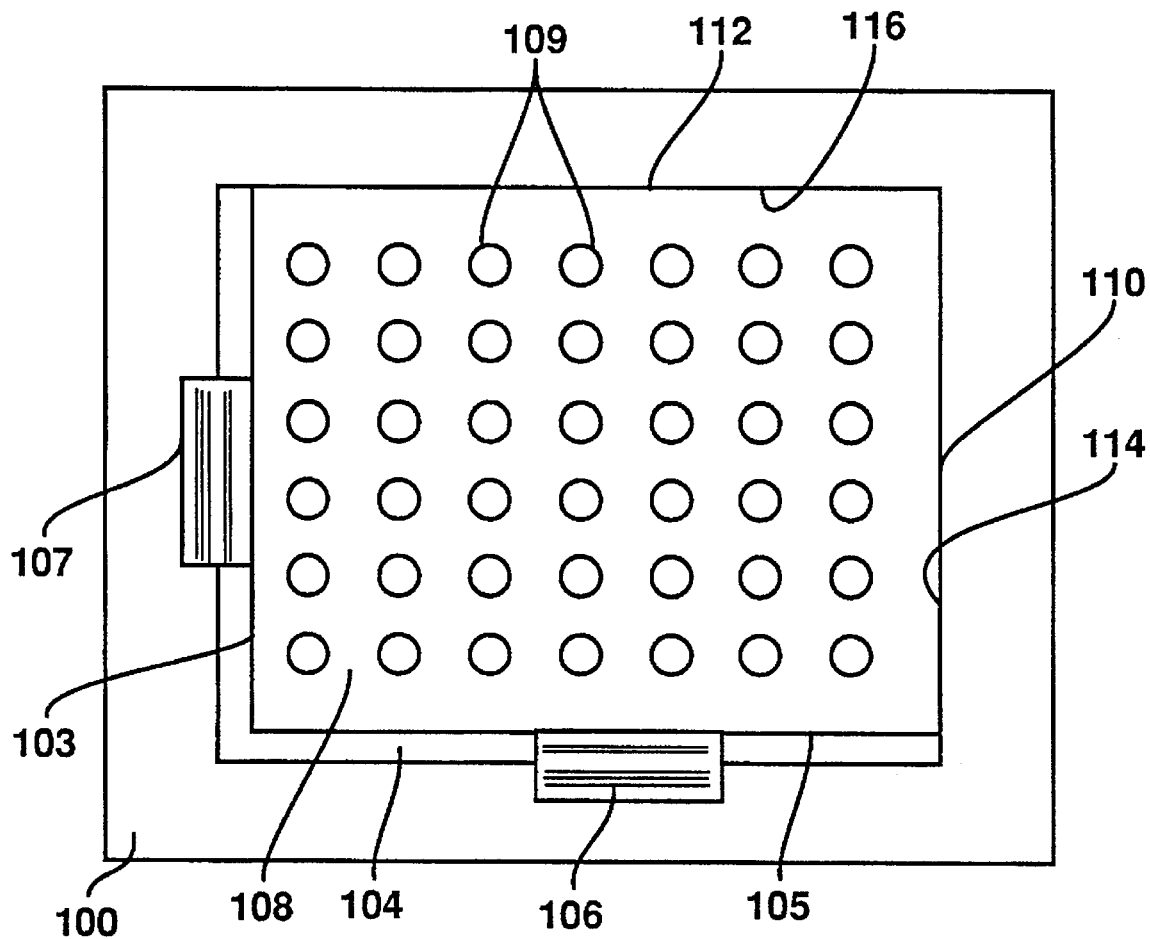
FIG. 2 is a top plan view of the prior-art mechanism of FIG. 1.
Figure 3:
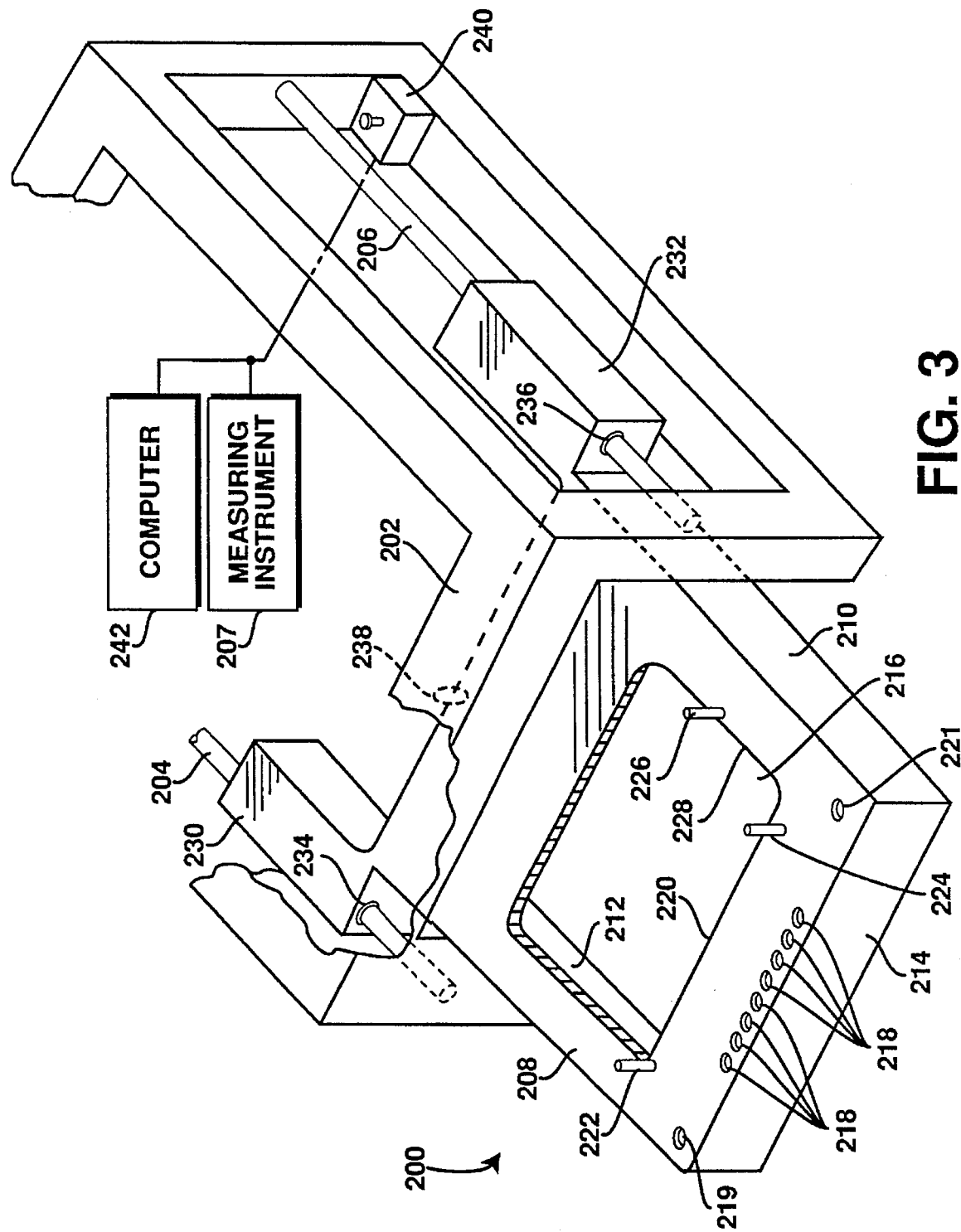
FIG. 3 is a perspective view of a loading carriage of the positioning mechanism according to the present invention.

The positioning mechanism according to the present invention includes a loading carriage 200, whose perspective view is shown in FIG. 3. Loading carriage 200 is slidingly mounted in a structure or enclosure 202 on parallel rails 204 and 206, rigidly attached to enclosure 202. Structure 202 also houses a measuring instrument 207 (shown schematically), e.g., a photometer, that assays analyte samples loaded into structure 202 by the positioning mechanism of the invention.

Loading carriage 200 comprises a flat plate 208, having side sections 210 and 212, as well as a front section 214, all formed orthogonally with respect to flat plate 208. A rectangular opening 216 is situated substantially at the center of flat plate 208. A portion of flat plate 208, bounded on one side by front section 214 and on the other side by an edge 220 of rectangular opening 216, contains a linear array of through circular openings 218. Guide pins 222 and 224, positioned on the flat plate 208 near front section 214 of loading carriage 200, are rigidly attached to flat plate 208. A third guide pin 226 is anchored to a portion of flat plate 208 delimited by side section 210 and an edge 228 of rectangular opening 216. Circular openings 219 and 221, used for light-intensity calibration, are formed in flat plate 208 so that the linear array of circular openings 218 is located there between.

Loading carriage 200 also includes supporting members 230 and 232. Supporting members 230 and 232 house linear bearings 234 and 236, respectively, allowing loading carriage 200 to translate along rails 204 and 206 with minimal friction. A stop pin 238 is located at the rear of loading carriage 200 and is positioned substantially in the middle of the loading carriage. An electric motor 240, attached to structure 202, effectuates linear motion of loading carriage 200 with respect to structure 202. Electric motor 240 is coupled to loading carriage 200 by a toothed-belt drive system (not shown) and is controlled by a computer 242 (shown schematically), which also governs the operation of measuring instrument 207 (shown schematically). The electric motor 240 may be used to move the loading carriage 200 into the structure 202 and to move the carriage 200 out of the structure 202. In this manner, the movement of the carriage 200 and any tray thereon may be automatically controlled by computer 242.

In one embodiment, the measuring instrument 207 may include an optical head of a spectrophotometer which is moved or scanned from analyte sample to analyte sample on a particular analyte receptacle (e.g. a microplate). An example of such a spectrophotometer is shown in U.S. patent application Ser. No. 08/100,541, which was filed Jul. 30, 1993, and is entitled "Multi-functional Photometer with Movable Linkage for Routing Optical Fibers," which is hereby incorporated by reference. In this case, it will be appreciated that repeatedly accurate alignment of an analyte receptacle and the analyte samples thereon relative to the optical head of the photometer will allow more accurate, reliable measurements and will allow the photometer to measure more samples per analyte receptacle because of the improved alignment of the receptacle and its samples relative to the optical head. It will also be understood that the photometer is typically secured to the structure 202 such that the photometer is aligned in space relative to the structure 202 and that once the receptacle 108 is aligned to the structure 202, the receptacle 108 will then be aligned relative to the photometer and its optical head.

In one particular embodiment of the present invention, flat plate 208 is approximately 15.5 cm wide and about 2 mm thick, and is made of aluminum. Guide pins 222, 224, 226, and stop pin 238 are made of stainless steel, each having a diameter of about 3.2 mm and a length of about 10.9 mm. Linear array of circular openings 218 comprises eight openings, each with a diameter of approximately 7 mm. Rectangular opening 216 measures roughly 11.5 cm by 8.0 cm.

Figure 4:
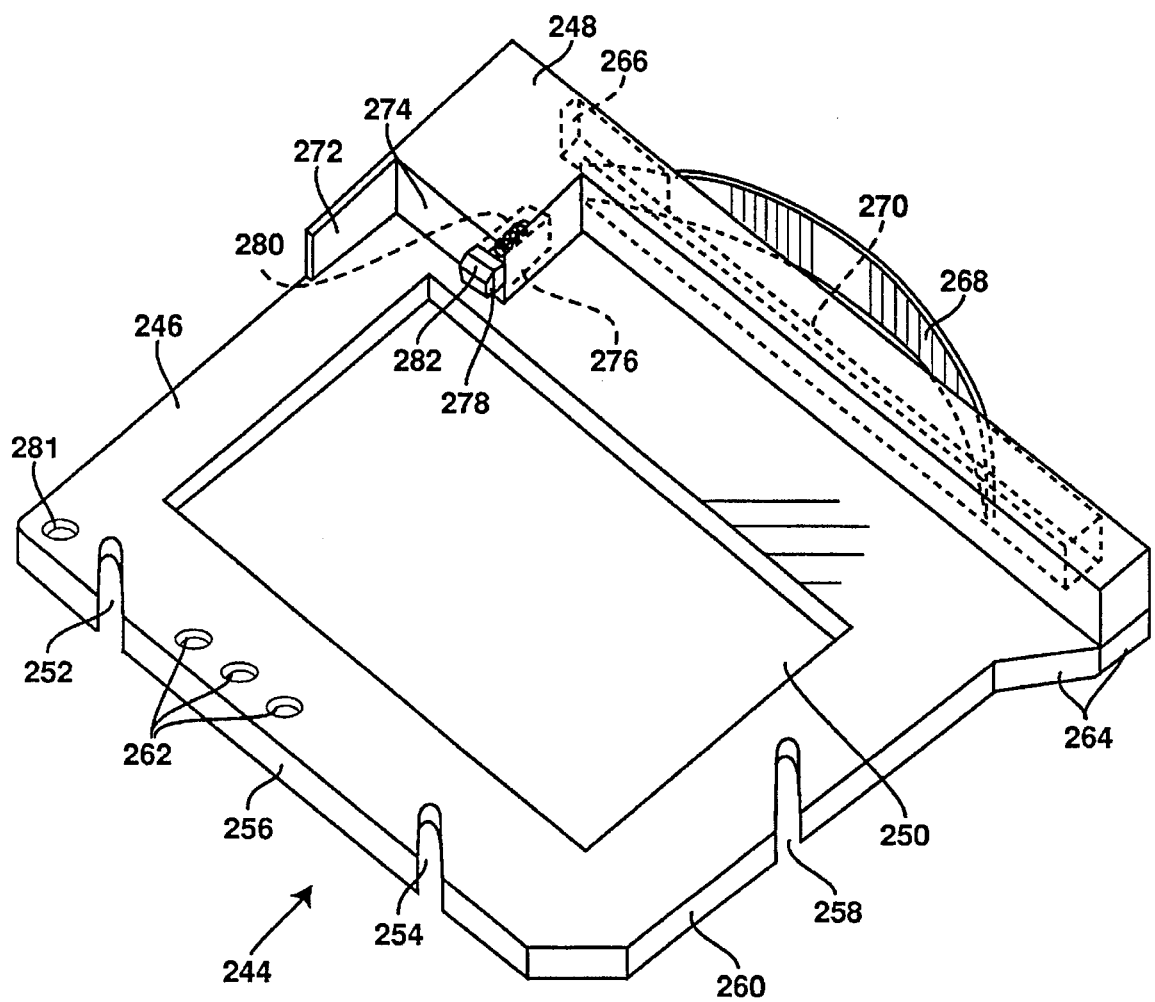
FIG. 4 is a perspective view of a tray of the positioning mechanism according to the present invention.

Loading carriage 200 bears a tray 244, illustrated in FIG. 4. Tray 244 includes a first portion 246 and a second portion 248. First portion 246 contains a rectangular opening 250, oblique slots 252 and 254 formed at a leading edge 256 of first portion 246, and an oblique slot 258 located at a lateral edge 260 of first portion 246. First portion 246 also has a linear array of through circular openings 262, positioned between oblique slots 252 and 254, and a contact protuberance 264, formed at the rear of tray. 244 and continuous with lateral edge 260. Oblique slots 252, 254, and 258 are parallel and have an angle of approximately 45° with respect to leading edge 256.

Second portion 248 includes a chamber 266 that houses a biasing device, e.g., a leaf spring 268, protruding from chamber 266 through a rectangular opening 270. Second portion 248 also defines orthogonal contact planes 272 and 274 and contains a cavity 276 that houses a contact element 278, preloaded by a helical spring 280, which is located inside cavity 276. Contact element 278 has a beveled top face 282, which projects through the opening of cavity 276, located in the surface of contact plane 274. An opening 281, used for light-intensity calibration and corresponding to opening 219, shown in FIG. 3, is formed to the outside of oblique slot 252. Opening 281 and opening 219 will typically be aligned together when the tray 244 is on the carriage 200 in the retracted position (when the carriage is within the structure 202); this alignment provides a hole through both the tray 244 and the carriage 200.

In one particular embodiment of the invention, rectangular opening 250 measures approximately 11.0 cm by 7.5 cm. Oblique slots 252, 254, and 258 are roughly 16.0 mm long and 3.25 mm wide. The array of circular openings 262 comprises three openings, each having a diameter of about 7 mm. Tray 244 is approximately 14.2 cm wide, 13.0 cm long, and from 0.6 to 2.2 cm thick.

OPERATION OF THE INVENTION

Figure 5:
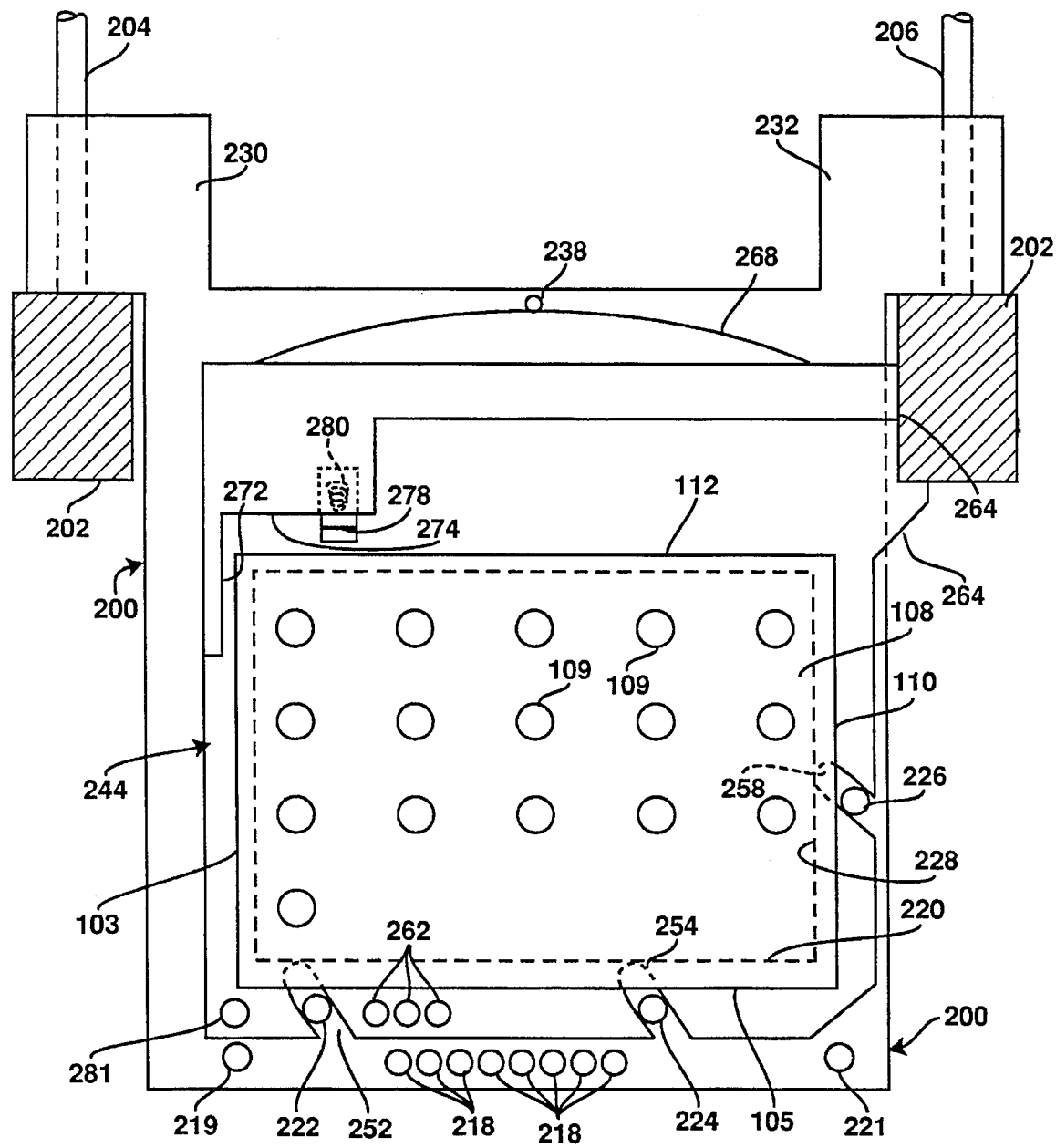
FIG. 5 is a top plan view of the positioning mechanism according to the present invention with the loading carriage of FIG. 3 in a protracted position.

As shown in FIG. 5, to insert analyte receptacle 108 into the positioning mechanism of the present invention, loading carriage 200 which carries tray 244 should be fully protracted from structure 202. The carriage 200 may be protracted by manual (e.g. by hand) or by automatic (e.g. by motor 240) movement of the carriage 200 along the rails 204 and 206. Analyte receptacle 108 is then simply placed onto tray 244.

The oblique slots of tray 244 are slidingly coupled with guide pins 222, 224, and 226 of loading carriage 200. It is apparent from FIG. 5 that, when loading carriage 200 is completely protracted from structure 202, protuberance 264 is in contact with structure 202, thus displacing tray 244 along guide pins 222, 224, and 226 to the left and rearward with respect to loading carriage 200 and preloading leaf spring 268 against stop pin 238. Contact of protuberance 264 with structure 202 prevents guide pins 222, 224, and 226 from fully engaging oblique slots 252, 254, and 258, thus providing an area defined by orthogonal contact planes 272 and 274 and guide pins 222, 224, and 226, which is greater than the area occupied by analyte receptacle 108. Because this area is greater than the surface area of the receptacle 108, it is possible to simply place the receptacle 108 onto tray 244 without any insertion force being required.

As is evident from the above description, robotic placement of analyte receptacle 108 in tray 244 is easily implemented since no force is required to insert analyte receptacle 108 into tray 244 and the area available for positioning analyte receptacle 108 is ample enough so that robotic mechanisms having a high degree of accuracy are not required.

As will be described in detail below, after analyte receptacle 108 is positioned in the above-described area, the loading carriage 200 is retracted into structure 202, causing analyte receptacle 108 to become automatically aligned so that analyte samples contained in wells 109 may be assayed by instrument 207 (schematically shown in FIG. 3).

Figure 6:
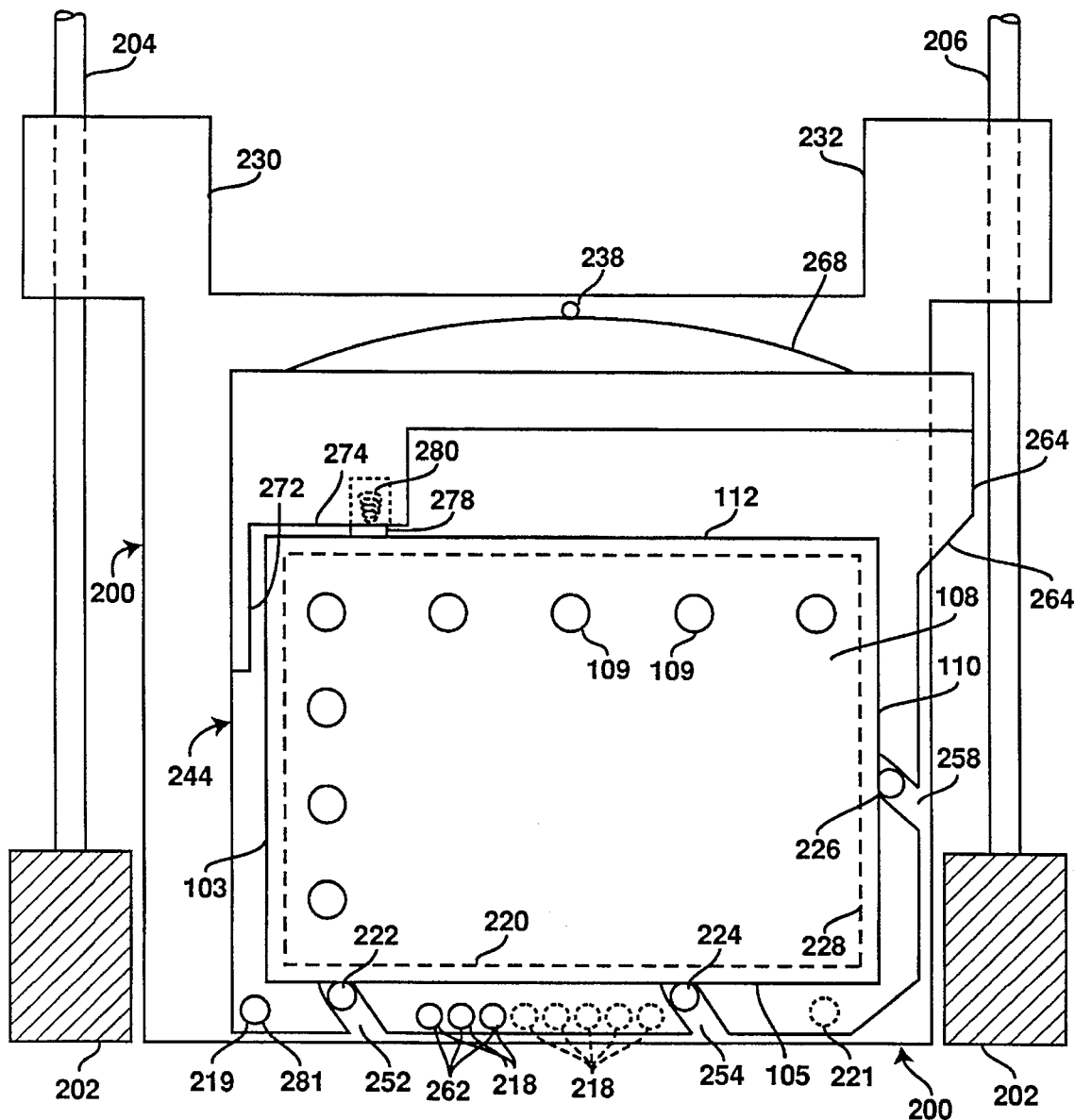
FIG. 6 is a top plan view of the positioning mechanism according of FIG. 5 with the loading carriage of FIG. 3 in a retracted position.

The automatic alignment of analyte receptacle 108 is illustrated in FIG. 6, which shows loading carriage 200 and tray 244 being fully retracted into the structure 202. As electric motor 240 (shown in FIG. 3), retracts loading carriage 200 into structure 202 along rails 204 and 206, contact between protuberance 264 of tray 244 and structure 202 is lost. This allows leaf spring 268, preloaded against stop pin 238, to displace tray 244 along guide pins 222, 224, and 226 to the right and forward with respect to loading carriage 200, fully engaging guide pins 222, 224, and 226 into oblique slots 252, 254, and 258, respectively. Such movement of tray 244 with respect to loading carriage 200 forces orthogonal contact planes 272 and 274 against the corner of analyte receptacle 108 defined by reference planes 103 and 112, thereby aligning reference planes 105 and 110 of analyte receptacle 108 with guide pins 222, 224, and 226. Furthermore, as contact element 278 touches reference plane 112 of analyte receptacle 108, helical spring 280 is compressed, preloading contact element 278 against reference plane 112 to insure proper alignment of analyte receptacle 108. Alternatively, leaf spring 268 and helical spring 280 may be replaced with other types of biasing devices, e.g., actuators or magnets having their same poles face each other.

The line contacts between guide pins 222, 224, and 226 and reference planes 105 and 110 of analyte receptacle 108 minimize misalignment problems associated with surface imperfections of reference planes 105 and 110. Moreover, extraneous particles of dirt and debris cannot easily accumulate between guide pins 222, 224, and 226 and reference planes 105 and 110 due to the small surface area of the line contacts and accordingly do not impair the accuracy of alignment.

When loading carriage 200 is fully retracted into structure 202 and reference planes 105 and 110 of analyte receptacle 108 are pressed against guide pins 222, 224, and 226 of loading carriage 200, circular openings 262 of tray 244 align with the corresponding circular openings 218 of loading carriage 200. Since the linear array of circular openings 262 contains fewer openings than the corresponding array of circular openings 218, some circular openings 218 will be blocked by the solid portion of tray 244. The resulting number and pattern of through openings define a binary code that enables computer 242 (shown in FIG. 3 and in FIG. 8) to recognize the well configuration of analyte receptacle 108 to be assayed, since a different number of circular openings 262 is formed in different versions of tray 244 for each particular configuration of analyte-receptacle wells. For example, tray 244 corresponding to an analyte receptacle having twenty four wells or sample locations may have three openings 262. Similarly, a tray 244 corresponding to an analyte receptacle having forty eight wells or sample locations may contain four openings, etc.

The binary code is generated when measuring instrument 207 (shown in FIG. 3) or another reading device (e.g. code reader 509 of FIG. 8) determines the pattern formed by overlapping arrays of circular openings 218 and 262. This may be performed by transmitting a light beam through one of the circular openings 218 from one side of the plate 208 determining whether the light beam was blocked by using a photodetector on the other side of the flat plate 208. It will be appreciated that other mechanisms may be employed to determine the code represented by the combination which results from a particular tray 244 and the loading carriage 200. The results of the determination are digitized in a conventional manner and then inputted into the computer (by, for example, an input/output controller such as the I/O controller 507 shown in FIG. 8).

Figure 8:
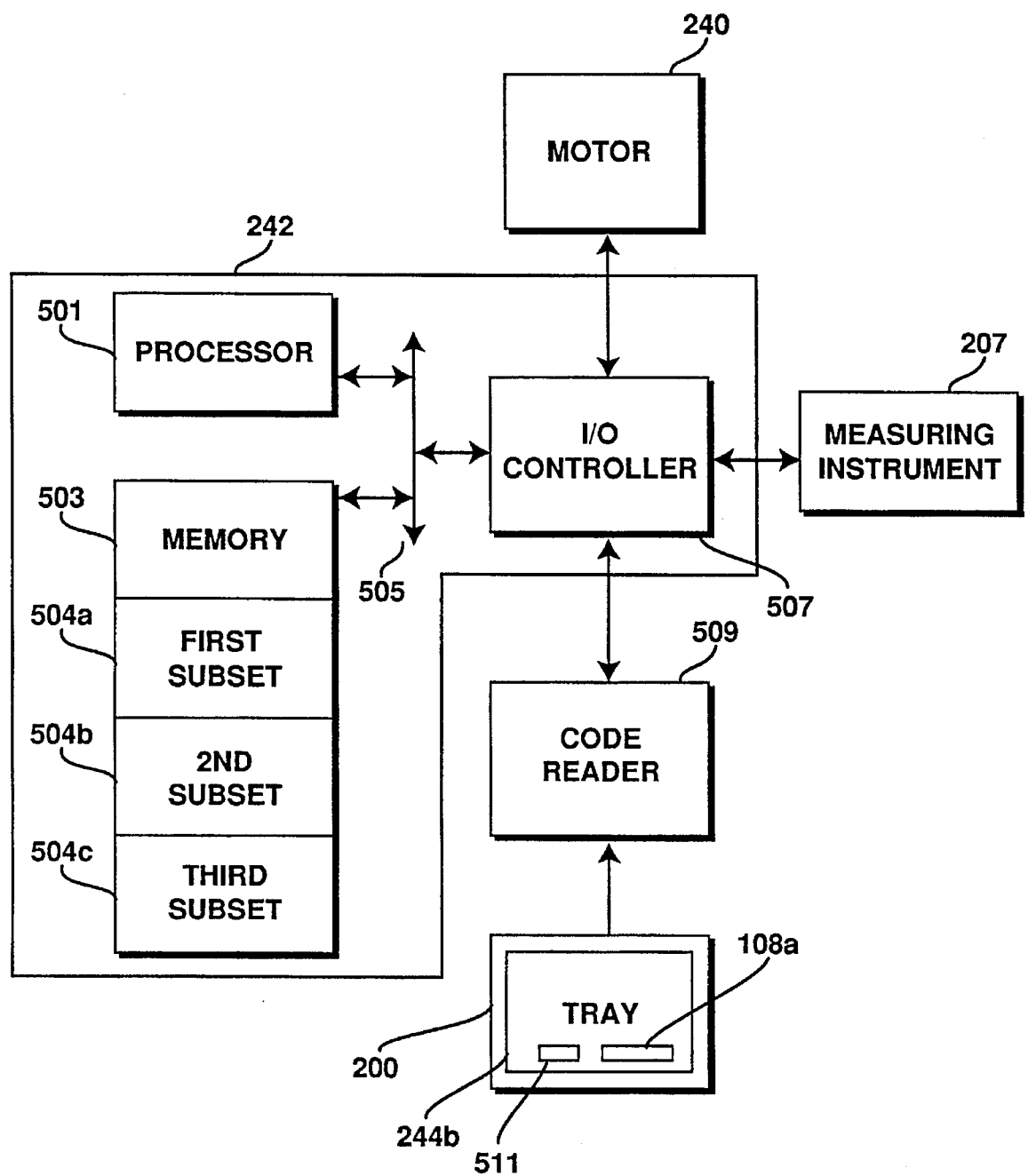
FIG. 8 shows a computer controlled code reader for determining automatically the particular analyte sample configuration on a particular tray.

Based on this digital information, computer 242 (shown in FIG. 3 and FIG. 8) selects a corresponding set of instructions stored in its memory 503 to control the appropriate measurement pattern for instrument 207 (shown in FIG. 3 and in FIG. 8). An example of a computer system which may control the measuring instrument is provided in U.S. patent application Ser. No. 08/325,043, which was filed Oct. 18, 1994 and is entitled "Method and Apparatus for Graphically Programming a Computer to Operate External Device" and is hereby incorporated by reference. The various possible configurations of a computer system are well known in the art; see, for example, those systems described in U.S. Pat. Nos. 4,942,606; 4,931,923; and 5,097,506. Such systems typically include memory (e.g. RAM) 503 for storing program instructions for controlling the operation of a processor 501 and peripherals coupled to the computer system through an input/output controller 507, where the memory 503, processor 501 (e.g. a microprocessor), and I/O controller 507 are coupled together by a bus 505. These program instructions may include several subsets of measuring instrument instructions for reading analyte receptacles. As shown in FIG. 8, each of the several subsets 504a, 504b and 504c may be selectively executed by processor 501 to control the measuring instrument 207 through the I/O controller 507. For example, subset 504a may correspond to a certain 48 well analyte receptacle, and such a tray and analyte receptacle combination may be placed on the carriage 200. Then, the code reader 509 (or, alternatively, the measuring instrument 207) reads the indicia 511 on the tray (or perhaps on the analyte receptacle) which represents the code that indicates that the analyte receptacle is the certain 48 well configuration. This code is then transmitted to the processor 501 through the I/O controller 507 and the processor 501 executes, in this example, the first subset 504a of measuring instrument instructions. It will be appreciated that code reader 509 (or the measuring instrument 207) may be controlled by the computer 242 during reading of the indicia 511 such that the user need only deposit the analyte receptacle on the tray (or directly on the carriage 200, depending on the embodiment) and instruct the computer 242 to retract the carriage 200 and read the indicia. Thereafter, the computer will control the sequence and manner of measurements automatically based on the indicia 511 determined in the process of the computer-controlled reading of the indicia.

It will be appreciated that, in one embodiment described above and in other embodiments, the leaf spring 268 is a biasing device which serves to bias certain alignment edges of the analyte receptacle 108 against alignment surfaces, such as guide pins 222, 224 and 226. In so doing, the biasing device keeps the analyte receptacle 108 securely aligned relative to the measuring instrument which is coupled to the structure 202. The contact protuberance 264 serves as a biasing disengagement device which disengages the biasing device when the analyte receptacle is to be inserted onto or removed from the loading carriage 200. For example, in one embodiment, when the loading carriage is protracted from the structure in order to insert the analyte receptacle 108 onto the loading carriage, the biasing disengagement device causes the biasing device to stop biasing the analyte receptacle 108 against the alignment surfaces. When the biasing device is disengaged by the biasing disengagement device, there is extra space on the loading carriage which will accommodate the analyte receptacle and allow the analyte receptacle to be inserted without any force. In certain embodiments, the biasing device and biasing disengagement device may be combined. An example of such a combination is an electromagnetic actuator which is spring-loaded or otherwise biased and then can be electrically disengaged by generating an electromagnetic field to disengage the biasing device. In certain other embodiments, the carriage may be fixed within a structure such that it is not retractably supported on rails, and the alignment surfaces are located on the carriage and engage the analyte receptacle without a tray to align it when the biasing device, also located on the carriage, is being engaged.

Figure 7:
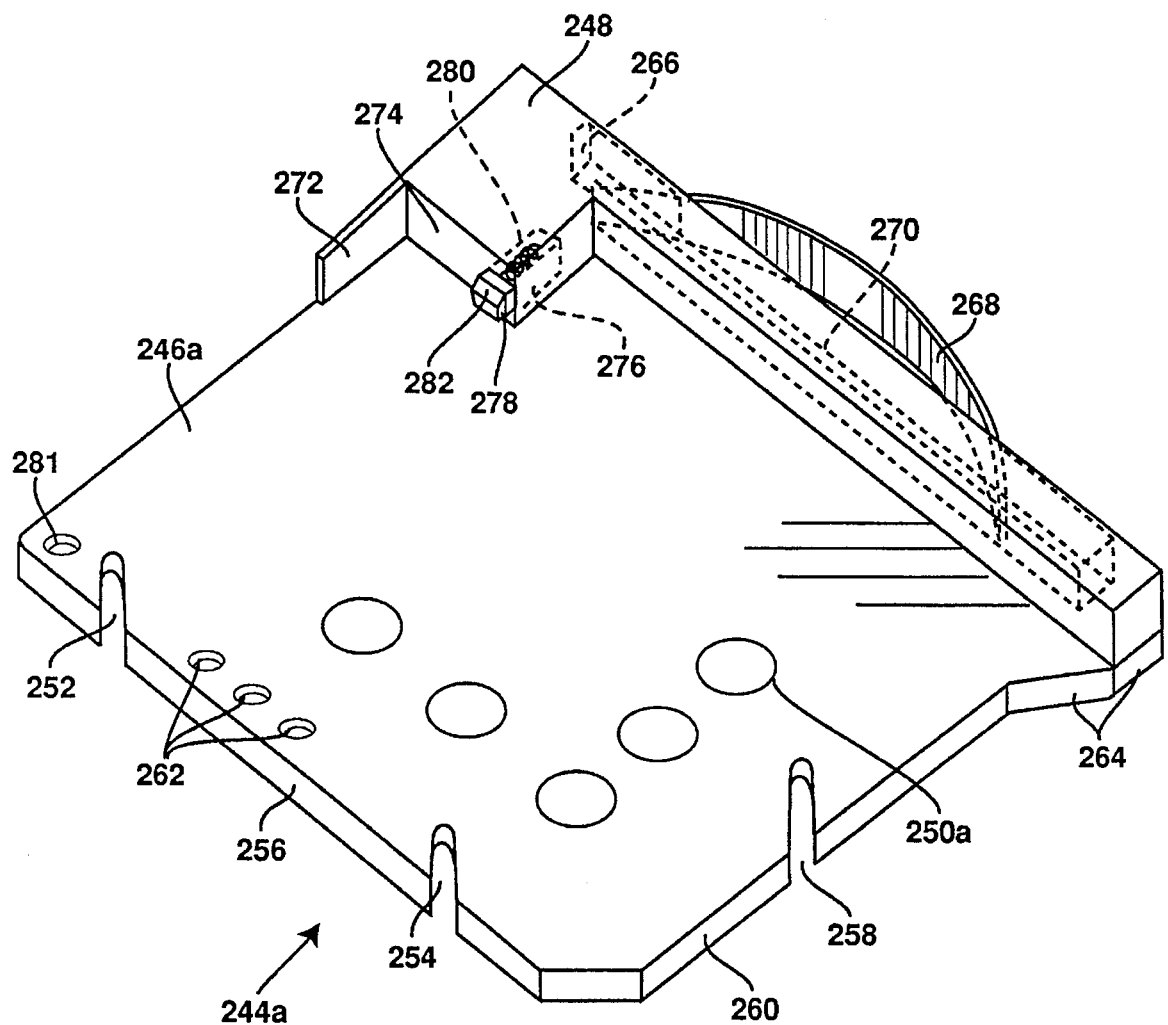
FIG. 7 is a perspective view of an alternative embodiment of the tray of FIG. 4.

Although the positioning mechanism of the present invention has been shown and described in the form of a specific embodiment, its configurations and materials are given only as examples, and many other modifications of the apparatus are possible. For example, instead of having rectangular opening 250, tray 244 could contain a plurality of openings 250a (as shown in FIG. 7), whose number and configuration would correspond to that of the sample locations of an analyte receptacle of one particular type with which that tray is designed to be used. The orientation and dimensions of oblique slots 252, 254, and 258 could vary. The positioning mechanism could be utilized for loading silicon wafers or electrophoresis gels as well as microplates. Depending on the type of assays measuring instrument 207 is designed to perform, loading carriage 200 and tray 244 may be manufactured without rectangular openings 216 and 250. The openings 262 may be replaced by indicators, such as a bar code which may be read by the measuring instrument 207 to determine the particular tray which is inserted and its corresponding analyte receptacle; alternatively, the tray may contain electrical contacts or diodes which may be electrically read by computer 242 to provide a code indicating the type of tray.

Thus, the invention, according to one possible embodiment, provides a positioning mechanism for specimens to be assayed by a measuring instrument, such as a photometer, where the positioning mechanism overcomes the foregoing drawbacks, e.g., requires no force for insertion therein of a receptacle containing the analyte samples to be assayed, allows such insertion to be reliably implemented by conventional and inexpensive robotic mechanisms, provides accurate alignment of the analyte receptacle with respect to the measuring instrument performing the assays and can be used without assuring that the surfaces (e.g. reference planes 103, 105, 110, and 112) of the analyte receptacle be clean of debris and without imperfections.

Another advantage of the present invention, in at least one possible embodiment, is the ability of the positioning mechanism to accommodate analyte receptacles of various configurations and to supply information about the configuration of a particular receptacle to a computer that controls the operation of the measuring instrument. This automatic recognition feature allows the user of the system to avoid having to explicitly instruct the system about the type of tray being used or the specific configuration of the analyte receptacle.

As demonstrated above, the invention may be practiced in numerous different embodiments and with various modifications. Therefore, the scope of the invention should be determined, not by the examples given, but by the appended claims and their equivalents.

What is claimed is:

1. A mechanism for positioning an analyte receptacle with respect to a measuring instrument, said mechanism comprising:
   a carriage retractably supported in a structure, said carriage includes at least three guide members and at least one stop member, rigidly attached to said carriage; and
   a tray movably coupled to said carriage, said tray comprises at least three slots capable of engaging said at least three guide members, at least one biasing device comprising a spring and being preloaded against said at least one stop member, a protuberance for contacting said structure, and a pair of contact surfaces capable of pushing said analyte receptacle against said at least three guide members, and wherein said tray is demountably coupled to said carriage, and wherein said protuberance contacts said structure when said carriage is protracted from said structure, thereby displacing said tray along said at least three guide members to provide an area for placing said analyte receptacle on said tray, said area being defined by said at least three guide members and said pair of contact surfaces.

2. The mechanism of claim 1 wherein said protuberance loses contact with said structure when said carriage is retracted into said enclosure, whereby said at least one biasing device displaces said tray along said at least three guide members such that said pair of contact surfaces pushes said analyte receptacle against said at least three guide members, thereby positioning said analyte receptacle so that its contents can be analyzed by said measuring instrument.

3. The mechanism of claim 2 wherein one of said contact surfaces contains a cavity having a compressibly preloaded contact element protruding therefrom.

4. The mechanism of claim 3 wherein said carriage further includes a first array of through openings, said tray having a second array of through openings, said analyte receptacle having a specific analyte-sample configuration, the number of the through openings in said second array corresponding to said specific analyte-sample configuration.

5. The mechanism of claim 4 wherein the through openings of said first and second arrays line up when said carriage is retracted into said enclosure, some of the through openings of said first array being blocked by said tray, resulting in a third array of through openings defining a binary code.

6. The mechanism of claim 5 wherein said carriage and said tray each have a through opening located substantially at the center thereof with nominal dimensions of said analyte receptacle and wherein said second array having fewer openings than said first array.

7. The mechanism of claim 5 wherein said carriage has a through opening located substantially at the center thereof with nominal dimensions of said analyte receptacle, said tray having an array of through openings substantially at the center thereof, said array of through openings having a configuration corresponding to said specific analyte-sample configuration of said analyte receptacle.

8. The mechanism of claim 5 further including a computer coupled to said measuring instrument, said computer stores a set of measuring-instrument instructions for reading said analyte receptacle, said set of measuring-instrument instructions comprising several subsets.

9. The mechanism of claim 8 wherein said at least one stop member and said at least three guide members comprise dowel pins.

10. The mechanism of claim 8 wherein said computer obtains said binary code by utilizing signals generated when said measuring instrument reads said third array of through openings, said computer executing a particular subset from said set of measuring-instrument instructions based on said binary code, said set of measuring-instrument instructions being stored in said computer.

11. A photometer having a mechanism for positioning an analyte receptacle with respect to said photometer, said photometer and said mechanism being coupled to a computer, said mechanism comprising:
    a carriage retractably supported in a structure; and
    a tray movably and demountably coupled to said carriage, wherein said tray comprises:
       three oblique slots slidingly engaging at least three guide pins on said carriage;
       a spring preloaded against at least one stop pin on said carriage; and
       a lateral protuberance contacting said structure when said carriage is
       protracted from said structure, thereby displacing
    said tray along said at least three guide pins to provide an area for placing said analyte receptacle on said tray, said area being defined by said at least three guide pins and a pair of vertical orthogonal contact surfaces formed on said tray.

12. The photometer of claim 11 wherein said lateral protuberance loses contact with said structure when said carriage is retracted into said structure, wherein said spring displaces said tray along said at least three guide pins so that said pair of vertical orthogonal contact surfaces pushes said analyte receptacle against said at least three guide pins, thereby positioning said analyte receptacle.

13. The photometer of claim 12 wherein said analyte receptacle comprises a plurality of analyte sites having a specific number and configuration, said carriage further including a first array of through openings, said tray having a second array of through openings, the number of openings in said second linear array corresponding to said specific number and configuration.

14. The photometer of claim 13 wherein the through openings of said first and second arrays line up when said carriage is retracted into said structure, some of the through openings of said first array being blocked by said tray, resulting in a third array of through openings defining a binary code.

15. The photometer of claim 14 wherein a computer obtains said binary code by utilizing the signals generated when said photometer reads said third array of through openings, said computer, based on said binary code, selecting a particular subset from an existing set of instructions for reading said analyte receptacle, said existing set of instructions being stored in said computer.

16. A method for positioning an analyte receptacle with respect to a measuring instrument, said method comprising:
   disengaging a biasing device on a structure to provide an opening between a plurality of alignment surfaces;
   placing said analyte receptacle on said structure;
   engaging said biasing device such that alignment edges of said analyte receptacle engage said plurality of alignment surfaces.

17. A method as in claim 16 wherein said step of placing occurs without requiring a force to overcome a corresponding force produced by said biasing device.

18. A method as in claim 16 wherein said step of disengaging said biasing device comprises moving a tray relative to said structure, said tray for holding said analyte receptacle.

19. A method as in claim 18 wherein said step of engaging said biasing device comprises moving said tray relative to said structure.

20. A method as in claim 16 wherein said step of engaging said biasing device comprises moving a tray relative to said structure, said tray for holding said analyte receptacle.

* * * * *